United States Patent [19]

Yamada et al.

[11] 4,237,227

[45] * Dec. 2, 1980

[54] PROCESS FOR PREPARING D-N-CARBAMOYL-α-AMINO ACIDS

[75] Inventors: Hideaki Yamada, Kyoto; Satomi Takahashi, Takatsuki; Koji Yoneda, Amagasaki, all of Japan

[73] Assignee: Kanegafuchi Kagaku Kogyo Kabushiki Kaisha, Osaka, Japan

[ * ] Notice: The portion of the term of this patent subsequent to Jun. 13, 1992, has been disclaimed.

[21] Appl. No.: 862,853

[22] Filed: Dec. 21, 1977

[30] Foreign Application Priority Data

Dec. 30, 1976 [JP] Japan ................................. 51/157713

[51] Int. Cl.³ ............................................. C12P 13/02
[52] U.S. Cl. .................................... 435/108; 435/106; 435/109; 435/110; 435/113; 435/115; 435/116; 435/129; 435/280
[58] Field of Search .................. 195/29; 435/280, 129, 435/106, 108, 109, 110, 113, 115, 116

[56] References Cited

U.S. PATENT DOCUMENTS

| | | | |
|---|---|---|---|
| 3,320,135 | 5/1967 | Okumura et al. | 195/29 |
| 3,494,831 | 2/1970 | Nakayama et al. | 195/29 |
| 4,016,037 | 4/1977 | Mitsugi et al. | 195/29 |
| 4,094,741 | 6/1978 | Yamada et al. | 195/29 |
| 4,111,749 | 9/1978 | Degen et al. | 195/29 |

OTHER PUBLICATIONS

Journal of the Agricultural Chemical Society of Japan, vol. 43, No. 8, pp. 528–535 (1969).

*Primary Examiner*—Alvin F. Tanenholtz
*Attorney, Agent, or Firm*—Armstrong, Nikaido, Marmelstein & Kubovcik

[57] ABSTRACT

A process for preparing D-N-carbamoyl-α-amino acids by subjecting 5-substituted hydantoins to the action of a cultured broth, cells or treated cells of microorganisms having an ability in asymmetrically hydrolyzing the hydantoin ring in an aqueous medium of pH 7 to 10. The process is suited for the industrial manufacture of D-N-carbamoyl-α-amino acids which are useful intermediates for the preparation of medicines.

8 Claims, No Drawings

PROCESS FOR PREPARING D-N-CARBAMOYL-α-AMINO ACIDS

BACKGROUND OF THE INVENTION

The present invention relates to a novel process for preparing D-N-carbamoyl-α-amino acids, and more particularly to a process for preparing D-N-carbamoyl-α-amino acids by biochemically hydrolyzing 5-substituted hydantoins by employing a cultured broth, cells or treated cells of microorganisms.

It is reported in FEBS LETTERS, Vol. 57, No. 2, 192(1975) that D-forms of N-carbamoyl-α-amino acids can be produced by subjecting DL-forms of 5-substituted hydantoins to the action of hydropyrimidine hydrase from calf liver. This process requires the use of the expensive enzyme.

There has never been known a process for converting 5-substituted hydantoins to D-forms of N-carbamoyl-α-amino acids by utilizing microorganisms. As only one instance of the formation of a D-N-carbamoyl-α-amino acid by microbial action, it is reported in Amino Acid and Nucleic Acid, No. 19, 48–56(1969) that when L-methionine was produced by culturing *Bacillus coagulans* in a culture medium containing DL-5-(2-methylthioethyl)hydantoin, D-N-carbamoylmethionine was by-produced. However, this process does not produce only D-N-carbamoyl-α-amino acid.

OBJECTS OF THE INVENTION

It is an object of the present invention to provide a novel process for preparing D-N-carbamoyl-α-amino acids from DL-, D- or L-forms of 5-substituted hydantoins by employing microbial enzymes.

A further object of the invention is to provide a process for economically preparing D-N-carbamoyl-α-amino acids in good yields.

Another object of the invention is to provide a process for preparing substances available as intermediates for preparing medicines.

These and other objects of the invention will become apparent from the description hereinafter.

DETAILED DESCRIPTION

It has now been found that the above-mentioned objects can be accomplished by subjecting 5-substituted hydantoins to the action of a cultured broth, cells or treated cells of microorganisms having an ability in asymmetrically hydrolyzing the hydantoin ring.

According to the present invention, D-forms of N-carbamoyl-α-amino acids can be advantageously prepared from 5-substituted hydantoins by the catalytic action of microbial enzymes which can be readily and inexpensively obtained. The reaction of the present invention may be represented as follows:

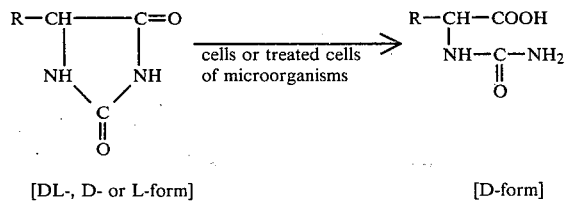

wherein R is an alkyl group, a substituted alkyl group, an aralkyl group, or a substituted aralkyl group.

The intracellular enzymes of microorganisms employed in the present invention selectively act on D-forms of 5-substituted hydantoins so as to hydrolyze them to cleave the hydantoin ring. Since the unhydrolyzed L-forms racemize in the reaction medium, the D-forms are always supplied in the reaction system in substance. Therefore, any of DL-, D- and L-forms of 5-substituted hydantoins can be employed in the present invention, and only D-forms of N-carbamoyl-α-amino acids can be obtained.

As mentioned before, it is reported that in the preparation of L-methionine from DL-5-(2-methylthioethyl)-hydantoin by the action of the particular bacteria, Bacillus coagulans, D-N-carbamoylmethionine was by-produced. However, according to the process of the present invention, only D-N-carbamoyl-α-amino acids are substantially produced from 5-substituted hydantoins without producing L-α-amino acids. The process of the invention is entirely different from the above reported process in the objects and effects, and further in the manner and conditions of the reaction. As stated above, the present invention relates to the process for the preparation of D-N-carbamoyl-α-amino acids by utilizing microorganisms, and in this point, is a new and useful process. Unlike a process employing enzymes obtained from internal organs of animals as mentioned before, the process of the invention is of great utility value for industrial manufacture in point of utilizing microorganisms obtained easily and inexpensively.

Also, it is well known that optically active N-carbamoyl-α-amino acids can be converted to optically active α-amino acids without changing configuration by reacting with nitrous acid. Therefore, by combining the process of the invention therewith, the industrially advantageous preparation of D-forms of α-amino acids has become possible. Since the importance of D-α-amino acids as intermediates for the preparation of antibiotics, peptide hormones, etc. is increasing in recent years, from this point of view the utility of the present invention is very great.

Any of DL-, D- and L-forms of the 5-substituted hydantoins can be employed in the present invention as the starting material. In case of the 5-substituted hydantoins which can be readily prepared by chemical synthesis, DL-forms are suitably employed. The DL-forms are prepared from the corresponding aldehydes by utilizing the Bucherer-Berg's method known as a synthetic method of α-amino acids. When L-α-amino acids are commercially available and can be inexpensively obtained, L-forms of the 5-substituted hydantoins which are derived from L-α-amino acids are suitably employed. L-forms of the 5-substituted hydantoins are derived from L-α-amino acids by reacting L-α-amino acids with potassium cyanate and then heating the produced L-N-carbamoyl-α-amino acids under an acidic condition to ring-close.

The 5-substituted hydantoins to which the process of the present invention is applicable are compounds in which a hydrogen atom at the 5-position of hydantoin is substituted by an alkyl group having 1 to 4 carbon atoms, an aralkyl group having 7 carbon atoms or those having a substituent group. The term "aralkyl group" as used herein means mainly benzyl group. The substituent groups attached to the alkyl or aralkyl group include a halogen atom, alkylthio group, hydroxy group, alkoxy group, cyano group, amino group, acylated amino group, indolyl group, imidazolyl group, carboxyl group and alkoxycarbonyl group. Examples of the 5-substituted hydantoins employed in the present invention are listed in Table 1 together with names of each α-amino acid corresponding thereto.

cleave" as used herein means an ability to hydrolyze the hydantoin ring of the 5-substituted hydantoins so as to substantially produce only D-forms of N-carbamoyl-α-

TABLE 1

| 5-Substituted hydantoin | Substituent group R of hydantoin | Corresponding α-amino acid |
|---|---|---|
| 5-Methylhydantoin | CH₃— | Alanine |
| 5-Chloromethyl-hydantoin | ClCH₂— | β-Chloroalanine |
| 5-Fluoromethyl-hydantoin | FCH₂— | β-Fluoroalanine |
| 5-Ethylhydantoin | CH₃CH₂— | α-Aminobutyric acid |
| 5-(n-Propyl)-hydantoin | CH₃CH₂CH₂— | Norvaline |
| 5-(iso-Propyl)-hydantoin | (CH₃)₂CH— | Valine |
| 5-(n-Butyl)-hydantoin | CH₃CH₂CH₂CH₂— | Norleucine |
| 5-(iso-Butyl)-hydantoin | (CH₃)₂CHCH₂— | Leucine |
| 5-(sec-Butyl)-hydantoin | CH₃CH₂(CH₃)CH— | Isoleucine and Alloisoleucine |
| 5-(2-Methylthio-ethyl)hydantoin | CH₃SCH₂CH₂— | Methionine |
| 5-(Hydroxyethyl)-hydantoin | HOCH₂— | Serine |
| 5-(Methoxymethyl)-hydantoin | CH₃OCH₂— | O-Methylserine |
| 5-(Hydroxyethyl)-hydantoin | HOCH₂CH₂— | Homoserine |
| 5-(1-Hydroxyethyl)-hydantoin | CH₃(HO)CH— | Threonine and Allothreonine |
| 5-Benzylhydrantoin | C₆H₅—CH₂— | Phenylalanine |
| 5-(4-Hydroxybenzyl)-hydantoin | HO—C₆H₄—CH₂— | Tyrosine |
| 5-(3-Aminopropyl)-hydantoin | H₂N—(CH₂)₃— | Ornithine |
| 5-(2-Cyanoethyl)-hydantoin | NC—(CH₂)₂— | γ-Cyano-α-aminobutyric acid |
| 5-(4-Aminobutyl)-hydantoin | H₂N—(CH₂)₄— | Lysine |
| 5-(3-Cyanopropyl)-hydantoin | NC—(CH₂)₃— | δ-Cyano-α-aminovaleric acid |
| 5-[4-(Benzoylamino)-butyl]hydantoin | C₆H₅—CONH—(CH₂)₄— | Benzoyllysine |
| 5-(Indolylmethyl)-hydantoin | (indolyl)—CH₂— | Tryptophan |
| 5-(Carboxylmethyl)-hydantoin | HOOC—CH₂— | Aspartic acid |
| 5-(2-Carboxyethyl)-hydantoin | HOOC—CH₂CH₂— | Glutamic acid |
| 5-[(2-methoxycarbonyl)ethyl]hydantoin | H₃COOC—CH₂CH₂— | γ-Methylglutamate |

The microorganisms employed in the present invention are those having an ability in asymmetrically hydrolyzing the hydantoin ring to cleave, and are selected by examining wild strains present in nature, strains deposited in public organizations and microorganisms obtained by artificial mutation from those strains for the presence of the above ability. The expression "ability in asymmetrically hydrolyzing the hydantoin ring to amino acids. As a method of examining for this ability, for instance, a method as stated below may be employed:

First, cells are collected by subjecting 2 ml. of a cultured broth of the microorganism to centrifugation, and then washed with 2 ml. of a 0.9% by weight saline water. Again, cells are collected by centrifugation. The thus obtained intact cells (wet weight: 40 to 400 mg.) are added to 2 ml. of a 0.1 to 1.0% by weight aqueous solution or suspension of the 5-substituted hydantoin. The reaction is then carried out at pH 7 to 10 at 30° to 40° C. for 10 to 40 hours. After the completion of the reaction, a concentrated hydrochloric acid solution of p-dimethylaminobenzaldehyde is added to the reaction mixture, and the resulting color-developed reaction mixture is subjected to centrifugation to remove insoluble materials such as cells. The amount of the produced N-carbamoyl-α-amino acid in the resulting supernatant liquid is then determined colorimetrically. With respect to the strain showing the relatively high conversion, the hydrolysis reaction of the 5-substituted hydantoin is again carried out on a large scale, and the produced N-carbamoyl-α-amino acid is isolated. Such strains as are confirmed to produce the D-forms of N-carbamoyl-α-amino acids and to scarcely by-produce the corresponding L-α-amino acids are adopted as the microorganisms employed in the present invention.

The microorganisms employed in the present invention are those passing the above examination, being selected from bacteria, actinomycetes, molds, yeasts and deuteromycetes. According to the research of the present inventors, such microorganisms can be found in a very wide range of the genus from the standpoint of taxonomy. For instance, examples of the bacteria are genera Achromobacter, Aerobacter, Aeromonas, Agrobacterium, Alcaligenes, Arthrobacter, Bacillus, Brevibacterium, Corynebacterium, Enterobacter, Erwinia, Escherichia, Klebsiella, Microbacterium, Micrococcus, Protaminobacter, Proteus, Pseudomonas, Sarcina, Serratia and Xanthomonas. Examples of the actinomycetes are genera Actinomyces, Actinoplanes, Mycobacterium, Nocardia and Streptomyces. Examples of the molds are genera Aspergillus, Paecilomyces and Penicillium. Examples of the yeasts are genera Candida, Pichia, Rhodotorula and Torulopsis.

The process of the present invention utilizes the catalytic action of an intracellular enzyme in the form of the cells or treated cells of microorganisms. The enzyme can be prepared by culturing a microorganism in a conventional manner. Although the culture is usually effected in a liquid medium, solid surface culture may also be employed. In general, carbon and nitrogen sources which microorganisms can assimilate and inorganic salt and other nutrients essential for the growth of the microorganisms are included in the culture medium. Preferably, a hydantoin compound such as hydantoin, DL-5-methylhydantoin and DL-5-(2-methylthioethyl)-hydantoin is added to the culture medium in an amount of 0.05 to 0.3% by weight to adaptively enhance the desired emzyme activity. The culture conditions are selected from the temperature range of 20° to 85° C. and pH range of 4 to 11 in accordance with the optimum growth conditions of the employed strain, and usually the microorganisms are cultured at a temperature of 20° to 40° C. at a pH of 5 to 9 for 10 to 75 hours. During the culture, the growth of the microorganism may be accelerated by aeration and agitation.

The thus cultured microorganisms are employed in the form of the cultured broth, cells or treated cells in the asymmetric hydrolysis of the 5-substituted hydantoins. In many cases, the reaction can be caused by employing the cultured broth containing the cells of microorganism as it is. However, in cases where components in the cultured broth are an obstacle to the reaction or where it is desired to increase the amount of cells, cells separated from the cultured broth are employed. Although the objects of the invention can be sufficiently attained by employing the intact cells, the cells may be employed in the form of the dried cells, for example, lyophilized cells and acetone powder, for the convenience of storage or handling. Also, the cells can be employed in the form of the treated cells, for example, crushed cells and cellular extract. Further, these cells and treated cells may be immobilized in a conventional manner.

The reaction substrate, i.e. 5-substituted hydantoin is usually admixed with the cultured broth, cells or treated cells in an aqueous medium to make the enzymes act catalytically on the substrate.

The concentration of the 5-substituted hydantoins is selected from 0.1 to 30% by weight. The solubility of the 5-substituted hydantoins in water is generally low, and in many cases, the 5-substituted hydantoins are present in a suspended form, but this is not an obstacle to the reaction since the substrate progressively dissolves into the aqueous reaction medium with the progress of the reaction.

The actual substrate for the microbial enzymes employed in the present invention is the D-forms of 5-substituted hydantoins, and only D-forms are selectively hydrolyzed to be converted to D-N-carbamoyl-α-amino acids. However, since in the reaction system there exists the racemization equilibrium as to the 5-substituted hydantoins, the unhydrolyzed L-forms are converted to the D-forms with the consumption of D-forms, and as a result, the D-forms are always supplied in the reaction system in substance. The L-forms are not actual substrate, but can be regarded as the indirect substrate, since the racemization reaction of the 5-substituted hydantoins proceeds in parallel with the enzymatic reaction. Therefore, any of DL-, D- and L-forms of the 5-substituted hydantoins can be employed as the starting material.

When carrying out the hydrolysis reaction of the 5-substituted hydantoins in an aqueous reaction medium, the reaction mixture is preferably maintained at pH 7 to 10. At this pH range, the desired products can be obtained in high yields as long as microorganisms having high activity are employed. When pH is lower than 7, the reaction rate is very slow. Also, when pH is higher than 10, side reactions may occur. At pH 7 to 10 the conversion rate of the DL- or L-forms of the 5-substituted hydantoin to D-N-carbamoyl-α-amino acids is remarkably increased, since the optimum pH of the microbial enzymes employed in the invention is near 8 to 9, the solubility of the substrate increases with increasing pH and the recemization of the hydantoin ring is effectively accelerated under alkaline conditions. With the progress of the reaction the pH of the reaction mixture decreases and, therefore, it is preferable to add at an appropriate time a neutralizing agent such as ammonia, caustic soda, caustic potash and sodium carbonate to the reaction mixture to maintain it at the optimum pH. Also, as occasion demands, an organic solvent and a surface active agent may be added to the reaction medium.

The hydrolysis reaction is carried out at a temperature suitable to the utilized microbial enzyme, and usually at a temperature of 20° to 85° C. The reaction time varies depending on the activity of the employed microorganism and the reaction temperature, and is usually selected from 5 to 100 hours.

The D-N-carbamoyl-α-amino acids produced by the hydrolysis reaction are isolated from the reaction mixture by pH adjustment or treatment with an ion-exchange resin. For instance, when the product is relatively hydrophobic like D-N-carbamoylmethionine and D-N-carbamoylphenylalanine, the reaction mixture is adjusted to pH 5 and is subjected to centrifugation or filtration to remove insoluble materials such as unchanged substrate and cells, and then the resulting supernatant liquid or filtrate is adjusted to pH 2 to 4 to precipitate the desired product. When the product is relatively hydrophilic like D-N-carbamoylserine and D-N-carbamoylalanine, the isolation is often conducted in such a manner as above with difficulty. In that case, the product is suitably isolated by the ion-exchange resin treatment. However, the ion-exchange resin treatment is not limited to such a case, and is available as a general isolating method. The product is adsorbed by passing the reaction mixture from which insoluble materials are previously removed, through a column of a basic anion-exchange resin, and then eluted from the anion-exchange resin with a solvent such as dilute hydrochloric acid. The eluate is then neutralized and concentrated under reduced pressure to recover crystals of the desired product.

D-N-carbamoyl-α-amino acids obtained by the process of the present invention are useful intermediates for preparing medicines. Further, in many cases, since it is known that D-N-carbamoyl-α-amino acids can be readily converted to D-α-amino acids by reacting with nitrous acid, D-α-amino acids can be advantageously prepared on an industrial scale by combining the process of the present invention with a known process.

The present invention is more particularly described and explained by means of the following Examples, in which all percents are percent by weight unless otherwise stated. These examples are intended to illustrate the invention and not to be construed to limit the scope of the invention.

Also, the microorganisms employed in the following examples are all previously known, and strains marked with IAM, IFO or ATCC are those deposited in the following depositories under the shown catalogue numbers.

IAM: Institute of Applied Microbiology, the University of Tokyo (Japan)
IFO: Institute for Fermentation, Osaka (Japan)
ATCC: American Type Culture Collection (U.S.A.)

EXAMPLE 1

The following liquid culture mediums (A) and (B) were prepared, and 100 ml. portions thereof were separately placed in 500 ml. shaking flasks and steam-sterilized at 120° C. for 15 minutes.

| Culture Medium (A) | | Culture Meduim (B) | |
|---|---|---|---|
| Meat extract | 2.0% | Meat extract | 0.5% |
| Glycerol | 0.6% | Peptone | 1.0% |
| Hydantoin | 0.1% | Yeast extract | 0.5% |
| pH | 5.5 | Hydantoin | 0.1% |
| | | NaCl | 0.15% |
| | | pH | 7.0 |

Pseudomonas striata IFO 12996 and Aerobacter cloacae IAM 1221, which had been previously cultured on a bouillon agar slant at 30° C. for 24 hours, were separately inoculated into the culture medium (A), and also Corynebacterium sepedonicum IFO 3306, which had also been previously cultured in the same manner as above, was inoculated into the culture medium (B). They were then cultured at 30° C. with shaking, for 18 hours for Pseudomonas striata IFO 12996 and Corynebacterium sepedonicum IFO 3306, and for 40 hours for Aerobacter cloacae IAM 1221. Cells were separated from each resulting cultured broth by centrifugation and washed with 100 ml. of a 0.9% saline water. The cells were collected again by centrifugation, and then suspended into 50 ml. of a 0.9% saline water. Each thus obtained cell suspension was employed as a component of the mixture described below.

The 5-substituted hydantoins shown in Table 2 were employed as the reaction substrate.

Mixture Components
(1) 1.0 ml. of aqueous substrate suspension in concentration of 100 mM which was prepared by suspending 5-substituted hydantoin into a 0.1 M $NaHCO_3$-$Na_2CO_3$ buffer solution of pH 9.5
(2) 1.0 ml. of cell suspension A ground stopper test tube was charged with the above components (1) and (2), and then the reaction was carried out at 33° C. for 20 hours with mild shaking. Immediately after the completion of the reaction, 0.5 ml. of a 10% aqueous solution of trichloroacetic acid, 0.5 ml. of a 10% solution of p-dimethylaminobenzaldehyde in 6 N hydrochloric acid and 3.0 ml. of pure water were added to the reaction mixture. The color-developed reaction mixture was centrifuged to remove insoluble materials and then subjected to the colorimetric determination of N-carbamoyl-α-amino acids at 420 nm. These reaction and determination procedures were repeated for each microorganism and each reaction substrate.

The amounts of N-carbamoyl-α-amino acids produced in the reaction mixtures and the conversions from 5-substituted hydantoins are shown in Table 2.

TABLE 2

| Reaction substrate | Product | Pseudomonas striata IFO 12996 | | Corynebacterium sepedonicum IFO 3306 | | Aerobacter cloacae IAM 1221 | |
|---|---|---|---|---|---|---|---|
| | | Amount mg./ml. | Conversion mole % | Amount mg./ml. | Conversion mole % | Amount mg./ml. | Conversion mole % |
| DL-5-methylhydantoin | N-carbamoyl-alanine | 3.0 | 46 | 2.6 | 40 | 3.6 | 55 |
| DL-5-(iso-propyl)hydantoin | N-carbamoyl-valine | 5.8 | 73 | 0.8 | 9.5 | 3.2 | 41 |
| DL-5-(iso-butyl)hydantoin | N-carbamoyl-leucine | 2.4 | 28 | 1.4 | 16 | 2.4 | 28 |
| DL-5-(2-methylthioethyl)-hydantoin | N-carbamoyl-methionine | 6.3 | 66 | 2.6 | 27 | 5.8 | 60 |
| L-5-(hydroxymethyl)-hydantoin | N-carbamoyl-serine | 4.6 | 62 | 2.5 | 33 | 2.0 | 27 |
| DL-5-benzylhydantoin | N-carbamoyl- | 1.2 | 12 | 2.2 | 21 | 0.2 | 1.9 |

TABLE 2-continued

| Reaction substrate | Product | Pseudomonas striata IFO 12996 | | Corynebacterium sepedonicum IFO 3306 | | Aerobacter cloacae IAM 1221 | |
|---|---|---|---|---|---|---|---|
| | | Amount mg./ml. | Conversion mole % | Amount mg./ml. | Conversion mole % | Amount mg./ml. | Conversion mole % |
| L-5-(carboxymethyl)-hydantoin | N-carbamoyl-aspartic acid | 0.32 | 3.6 | 0.25 | 2.8 | 0.2 | 2.2 |
| L-5-(2-carboxyethyl)-hydantoin | N-carbamoyl-glutamic acid | 0.38 | 4.0 | 0.21 | 2.2 | 0.0 | 0.0 |
| DL-5-(4-aminobutyl)-hydantoin | N-carbamoyl-lysine | 0.72 | 7.6 | 0.34 | 3.6 | 0.88 | 9.3 |

EXAMPLE 2

By employing the same microorganisms as those employed in Example 1, the hydrolysis reaction of the 5-substituted hydantoins shown in Table 3 was carried out on a larger scale than that in Example 1 as follows:

The culture of the microorganisms was conducted in the same manner as in Example 1 except that 500 ml. portions of the culture medium (A) or (B) were separately placed in 2 liter shaking flasks. From each resulting cultured broth, cells were separated by centrifugation and washed with 500 ml. of a 0.9% saline water. The cells were collected again by centrifugation, and then suspended into 100 ml. of a 0.9% saline water. Each thus obtained cell suspension was employed as a component of the mixture described below.

Mixture Components
(1) 1.0 g. of 5-substituted hydantoin
(2) 80 ml. of 0.1 M NaHCO$_3$—Na$_2$CO$_3$ buffer solution of pH 9.5
(3) 20 ml. of cell suspension The mixture of the above components (1), (2) and (3) was placed in a 300 ml. ground stopper Erlenmeyer flask, and the reaction was carried out at 33° C. for 20 hours with mild shaking. During the reaction, the mixture was maintained at pH 8.5 to 9.0 by adding 2 N NaOH at an appropriate time.

After the completion of the reaction, the reaction mixture was adjusted to pH 5.0 and then centrifuged to remove insoluble materials such as unaltered substrate and cells. The resulting supernatant solution was lyophilized, and the obtained powders were extracted with ethanol. After adding 5 g. of silica-gel to the extract, ethanol was distilled away. The residue was packed in a column and then silica-gel column chromatography was applied for the purification. The column was first eluted by acetone and then by ethanol. The product was obtained by distilling away the solvent from the fraction containing N-carbamoyl-α-amino acid. When the purification was still insufficient, the purification was further carried out by employing an acetate-type anion-exchange resin (commercially available under the registered trademark "Amberlite IRA-400" made by Rohm & Haas Co.). After eluting with 1.5 to 2 M acetic acid, the eluate was lyophilized to give the product of higher purity.

The above procedures were made on all microorganisms and substrates.

The results of the amount, melting point and specific rotatory power of the obtained N-carbamoyl-α-amino acids are shown in Table 3.

Also, the results of the elemental analysis and infrared spectrum of the products were theoretically reasonable. It was confirmed from the results of silica-gel thin layer chromatograms (solvent: n-butanol/acetic acid/water = 4/1/1) that the purity was high, and from the values of the specific rotatory power that all products were the D-forms.

TABLE 3

| Strain | Substrate | Product | Yield mg. | Melting point °C. | Specific rotatory power $[\alpha]_D^{25}$ |
|---|---|---|---|---|---|
| Pseudomonas striata IFO 12996 | DL-5-methylhydantoin | D-N-carbamoyl-alanine | 395 | 177–179 | −20.5° (c = 2.0, 1N NH$_4$OH) |
| | DL-5-(iso-butyl)hydantoin | D-N-carbamoyl-leucine | 105 | 206–208 | −0.66° (c = 1.8, 1N NH$_4$OH) |
| | L-5-(hydroxymethyl)-hydantoin | D-N-carbamoyl-serine | 563 | 140–141 | −33.4° (c = 2.8, 1N NH$_4$OH) |
| Corynebacterium sepedonicum IFO 3306 | DL-5-methylhydantoin | D-N-carbamoyl-alanine | 310 | 177–179 | −19.6° (c = 1.6, 1N NH$_4$OH) |
| | DL-5-benzylhydantoin | D-N-carbamoyl-phenylalanine | 205 | 199–200 | −37.5° (c = 2.0, 1N NH$_4$OH) |
| Aerobacter cloacae IAM 1221 | DL-5-methylhydantoin | D-N-carbamoyl-alanine | 408 | 175–178 | −17.8° (c = 1.9, 1N NH$_4$OH) |
| | DL-5-(isopropyl)hydantoin | D-N-carbamoyl-valine | 355 | 211–213 | −14.0° (c = 2.6, 1N NH$_4$OH) |

EXAMPLE 3

Microorganisms shown in Table 4 were inoculated onto bouillon agar slants from type culture collections and cultured at 33° C. for 24 hours.

A liquid medium of pH 7.0 containing the following components was prepared, and 10 ml. portions thereof were placed in test tubes and were steam-sterilized at 120° C. for 10 minutes.

| Medium Components | |
|---|---|
| Meat extract | 0.5% |
| Yeast extract | 0.5% |
| Peptone | 1.0% |
| Hydantoin | 0.1% |
| NaCl | 0.15% |

Each microorganism which had grown on the bouillon agar slants was inoculated into the liquid medium in each test tube with a platinum loop. After culturing at 33° C. for 24 hours with shaking, cells were separated from each resulting cultured broth by centrifugation and was washed with 10 ml. of a 0.9% saline water. The cells were collected again by centrifugation, and then suspended into 3.3 ml. of a 0.9% saline water. Each thus obtained suspension was employed as a component of the mixture described below.

Mixture Components
(1) 3.3 ml. of aqueous substrate suspension of pH 7.6 containing 3.0% of DL-5-(2-methylthioethyl)-hydantoin
(2) 3.3 ml. of 0.2 M phosphate buffer solution of pH 7.6
(3) 3.3 ml. of cell suspension A test tube was charged with the above components (1), (2) and (3), and the reaction was then carried out at 33° C. for 40 hours with mild shaking. After the completion of the reaction, 2.0 ml. of the reaction mixture was taken and then subjected to the colorimetric determination of N-carbamoylmethionine in the same manner as in Example 1. The same procedure was repeated for each microorganism.

The amounts of N-carbamoylmethionine produced in the reaction mixtures and the conversions from DL-5-(2-methylthioethyl)hydantoin are shown in Table 4.

TABLE 4

| Strain | Amount of N-carbamoyl-methionine mg./ml. | Conversion mole % |
|---|---|---|
| Achromobacter delmarvae IFO 12668 | 1.9 | 17 |
| Aerobacter cloacae IAM 1221 | 4.6 | 42 |
| Aeromonas hydrophila IFO 3820 | 0.3 | 3 |
| Agrobacterium rhizogenes IFO 13259 | 3.4 | 31 |
| Alcaligenes faecalis IFO 13111 | 0.2 | 2 |
| Arthrobacter simplex IFO 12069 | 0.6 | 5 |
| Bacillus sphaericus IFO 3525 | 0.3 | 3 |
| Brevibacterium incertum IFO 12145 | 2.2 | 20 |
| Corynebacterium sepedonicum IFO 3306 | 4.2 | 38 |
| Enterobacter cloacae IFO 13535 | 0.1 | 1 |
| Erwinia aroidiae IFO 12380 | 0.1 | 1 |
| Escherichia coli ATCC 21148 | 0.1 | 1 |
| Klebsiella pneumoniae IFO 3319 | 0.2 | 2 |
| Microbacterium flavum ATCC 10340 | 1.5 | 14 |
| Micrococcus roseus IFO 3764 | 2.3 | 21 |
| Mycobacterium smegmatis ATCC 607 | 3.6 | 33 |
| Nocardia corallina IFO 3338 | 3.9 | 36 |
| Protaminobacter alboflavus IFO 3707 | 0.2 | 2 |
| Proteus morganii IFO 3848 | 0.3 | 3 |
| Pseudomonas chlororaphis IFO 3904 | 3.8 | 35 |
| Pseudomonas striata IFO 12996 | 5.3 | 48 |
| Sarcina marginata IFO 3066 | 0.3 | 3 |
| Serratia plymuthicum IFO 3055 | 0.1 | 1 |
| Xanthomonas campestris IAM 1671 | 0.1 | 1 |

EXAMPLE 4

The hydrolysis of DL-5-(2-methylthioethyl)hydantoin was carried out by employing the microorganisms shown in Table 5.

The following liquid culture medium of pH 7.0 was prepared, and 300 ml. portions thereof were separately placed in 2 liter shaking flasks and were steam-sterilized at 120° C. for 10 minutes.

| Medium Components | |
|---|---|
| Meat extract | 1.0% |
| Yeast extract | 0.5% |
| Peptone | 1.0% |
| DL-5-(2-methylthioethyl)hydantoin | 0.3% |
| NaCl | 0.3% |

Each microorganism previously cultured on a bouillon agar slant at 33° C. for 24 hours was inoculated into the liquid culture medium in the shaking flask, and was cultured at 33° C. for 22 hours with shaking. Cells were separated from each resulting cultured broth by centrifugation and washed with 150 ml. of a 0.9% saline water. The cells were collected again by centrifugation, and then suspended into 50 ml. of a 0.9% saline water. Each thus obtained cell suspension was employed as a component of the mixture described below.

Mixture Components
(1) 33 ml. of aqueous substrate suspension of pH 7.6 containing 3.0% of DL-5-(2-methylthioethyl)-hydantoin
(2) 33 ml. of 0.2 M phosphate buffer solution of pH 7.6
(3) 33 ml. of cell suspension The mixture of the above components (1), (2) and (3) was placed in a 300 ml. ground stopper Erlenmeyer flask, and the reaction was then carried out at 33° C. for 64 hours with mild shaking.

After the completion of the reaction, the reaction mixture was adjusted to pH 5.5 and then centrifuged to remove insoluble materials such as unaltered substrate and cells. The resulting supernatant solution was lyophilized, and the obtained powder was extracted with ethanol. After adding 5 g. of silica-gel to the extract, ethanol was distilled away. The residue was packed in a column and then silica-gel column chromatography was applied for the purification. The column was first eluted by acetone and then by methanol. The fraction containing N-carbamoylmethionine was taken and the solvent was distilled away to give powders. The powders were then subjected to the recrystallization from an ethanol-water solvent to give N-carbamoylmethionine of high purity.

The above reaction and purification procedures were repeated for each microorganism.

The results of the amount, melting point and specific rotatory power of the obtained N-carbamoylmethionine are shown in Table 5.

It was confirmed from the results of specific rotatory power that all of the obtained N-carbamoylmethionine were the D-form.

Also, the results of the elemental analysis and infrared spectrum of the product were theoretically reasonable. It was also confirmed from the results of silica-gel thin layer chromatograms (solvent: n-butanol/acetic acid/water=4/1/1) that the purity was high.

TABLE 5

| Strain | Yield mg. | Melting point °C. | Specific rotatory power $[\alpha]_D^{25}$ |
|---|---|---|---|
| Aerobacter chloacae IAM 1221 | 305 | 159–162 | +23.4° (c = 2, 5N HCl) |
| Agrobacterium rhizogenes IFO 13259 | 95 | 159–161 | +23.1° (c = 2, 5N HCl) |
| Corynebacterium sepedonicum IFO 3306 | 137 | 158–162 | +20.4° (c = 2, 5N HCl) |
| Mycobacterium smegmatis ATCC 607 | 215 | 160–162 | +23.5° (c = 2, 5N HCl) |

TABLE 5-continued

| Strain | Yield mg. | Melting point °C. | Specific rotatory power $[\alpha]_D^{25}$ |
|---|---|---|---|
| *Pseudomonas striata* IFO 12996 | 330 | 160-162 | +24.2° (c = 2, 5N HCl) |

EXAMPLE 5

A liquid culture medium of pH 7.0 containing the following components was prepared, and 10 ml. portions thereof were placed in test tubes and were steam-sterilized at 120° C. for 10 minutes.

| Medium Components | |
|---|---|
| Glucose | 2.0% |
| Soybean meal | 1.0% |
| Yeast extract | 0.25% |
| $(NH_4)_2SO_4$ | 0.1% |
| $CaCO_3$ | 0.5% |
| $K_2HPO_4$ | 0.4% |
| DL-5-(2-methylthioethyl)hydantoin | 0.3% |

Microorganisms shown in Table 6 were inoculated onto bouillon agar slants from type culture collections and previously cultured at 30° C. for 70 hours. The obtained cells were separately inoculated into the liquid culture mediums in test tubes with a platinum loop. After culturing at 30° C. for 72 hours with shaking, the obtained broths were treated in the same manner as in Example 3 to give cell suspensions. By employing the thus obtained cell suspensions, the hydrolysis of DL-5-(2-methylthioethyl)hydantoin was carried out at 33° C. for 40 hours in the same manner as in Example 3. Also, the amounts of N-carbamoylmethionine produced in the reaction mixture and the conversions from DL-5-(2-methylthioethyl)hydantoin were obtained in the same manner as in Example 3.

The results are shown in Table 6.

TABLE 6

| Strain | Amount of N-carbamoyl-methionine mg./ml. | Conversion mole % |
|---|---|---|
| *Actinomyces griseoruber* IFO 12872 | 0.8 | 7 |
| *Actinoplanes philippiensis* IAM 0120 | 4.2 | 38 |
| *Streptomyces almquisti* ATCC 618 | 3.0 | 27 |
| *Streptomyces aureus* IFO 3175 | 1.4 | 13 |
| *Streptomyces flaveolus* IFO 3408 | 1.1 | 10 |
| *Streptomyces griseus* ATCC 10137 | 2.3 | 21 |

The reaction was then carried out on a larger scale by employing Actinoplanes philippiensis IAM 0120 and Streptomyces alumquisti ATCC 618 respectively as follows:

Each broth of the microorganism which had been previously cultured in 10 ml. of the before-mentioned liquid culture medium, was admixed with each 90 ml. of the same culture medium and then the culture was carried out. After separating cells from each resulting cultured broth and washing with a 0.9% saline water, cells were suspended into 33 ml. of a 0.9% saline water to give cell suspensions which were employed as a component of the mixture described below.

Mixture Components (1) 33 ml. of aqueous substrate suspension of pH 7.6 containing 3.0% of DL-5-(2-methylthioethyl)-hydantoin (2) 33 ml. of 0.2 M phosphate buffer solution of pH 7.6

(3) 33 ml. of cell suspension

A 300 ml. ground stopper Erlenmeyer flask was charged with the above components (1), (2) and (3), and then the reaction was carried out at 33° C. for 40 hours with mild shaking. After the completion of the reaction, crystals of high purity were obtained by treating the reaction mixture in the same manner as in Example 4.

The results of the amount and specific rotatory power of the obtained N-carbamoylmethionine are shown in Table 7.

It was confirmed from the results of the specific rotatory power that the product was the D-form. Also, the results of the elemental analysis and infrared spectrum were theoretically reasonable. It was also confirmed from the results of silica-gel thin layer chromatogram (solvent: n-butanol/acetic acid/water=4/1/1) that the purity was high.

TABLE 7

| Strain | Yield mg. | Specific rotatory power $[\alpha]_D^{25}$ |
|---|---|---|
| *Actinoplanes philippiensis* IAM 0120 | 280 | +23.7° (c = 2, 5N HCl) |
| *Streptomyces alumquisti* ATCC 618 | 205 | +24.0° (c = 2, 5N HCl) |

EXAMPLE 6

A liquid medium of pH 7.6 containing the following components was prepared, and 10 ml. portions thereof were placed in test tubes and were steam-sterilized at 120° C. for 10 minutes.

| Medium Components | |
|---|---|
| Sucrose | 10.0% |
| Yeast extract | 0.2% |
| $(NH_4)_2HPO_4$ | 0.2% |
| $KH_2PO_4$ | 0.1% |
| $MgSO_4 \cdot 7H_2O$ | 0.1% |
| $CaCO_3$ | 0.2% |
| DL-5-(2-methylthioethyl)hydantoin | 0.2% |

Each microorganism shown in Table 8, which had been previously cultured on a malt agar slant at 30° C. for 24 hours, was inoculated into each culture medium with a platinum loop and was cultured at 30° C. for 40 hours with shaking. Cells were separated from each of the resulting cultured broths by centrifugation and then treated in the same manner as in Example 3 to give cell suspensions.

By employing the thus prepared cell suspensions, the hydrolysis of DL-5-(2-methylthioethyl)hydantoin was carried out at 33° C. for 40 hours and the analysis was then carried out, in the same manner as in Example 3.

The amounts of N-carbamoylmethionine produced in the reaction mixture and the conversions from DL-5-(2-methylthioethyl)hydantoin are shown in Table 8.

TABLE 8

| Strain | Amount of N-carbamoyl-methionine mg./ml. | Conversion mole % |
|---|---|---|
| Candida utilis IAM 4220 | 0.3 | 3 |
| Candida macedoniensis IFO 0706 | 0.2 | 2 |
| Pichia vini IFO 0795 | 0.1 | 1 |
| Rhodotorula glutinis IFO 0559 | 0.6 | 5 |
| Torulopsis utilis IAM 4246 | 0.1 | 1 |

EXAMPLE 7

A liquid medium of pH 6.0 containing the following components was prepared, and 10 ml. portions thereof were placed in test tubes and were steam-sterilized at 120° C. for 10 minutes.

| Medium Components | |
|---|---|
| Glucose | 10.0% |
| Peptone | 0.2% |
| $KNO_3$ | 0.2% |
| $(NH_4)H_2PO_4$ | 1.0% |
| $MgSO_4 \cdot 7H_2O$ | 0.05% |
| $CaCl_2$ | 0.01% |
| DL-5-(2-methylthioethyl)hydantoin | 0.2% |

Each microorganism shown in Table 9, which had been previously cultured on a Bennett's agar slant at 28° C. for 70 hours, was inoculated into the liquid culture medium with a platinum loop, and was cultured at 26° C. for 40 hours with shaking. Cells were separated from each of the resulting cultured broths by centrifugation, and then cell suspensions were prepared in the same manner as in Example 3.

The hydrolysis reaction of DL-5-(2-methylthioethyl)hydantoin and the colorimetric determination of the produced N-carbamoylmethionine were carried out in the same manner as in Example 3.

The results are shown in Table 9.

TABLE 9

| Strain | Amount of N-carbamoylmethionine mg./ml. | Conversion mole % |
|---|---|---|
| Aspergillus nigar IAM 3009 | 0.2 | 2 |
| Paecilomyces varioti IFO 5476 | 0.4 | 4 |
| Penicillium citrinum IFO 6352 | 0.1 | 1 |

EXAMPLE 8

A liquid medium containing the following components was prepared, and 10 ml. portions thereof were placed in large test tubes.

| Medium Components | |
|---|---|
| Meat extract | 0.5% |
| Yeast extract | 0.5% |
| $KH_2PO_4$ | 0.2% |
| $MgSO_4 \cdot 7H_2O$ | 0.1% |
| $CaCl_2 \cdot 2H_2O$ | 40 p.p.m. |

Hydantoin, DL-5-methylhydantoin and DL-5-(2-methylthioethyl)hydantoin were separately added to each test tube, respectively in an amount of 20 mg. (concentration: 0.2%). After adjusting to pH 7.0, each culture medium was steam-sterilized at 120° C. for 15 minutes, and Pseudomonas striata IFO 12996 was inoculated into it with a platinum loop. The culture was then carried out at 30° C. for 16 hours with shaking. Cells were separated from each resulting cultured broth by centrifugation and was washed with 10 ml. of a 0.9% saline water. The cells were collected again by centrifugation, and then suspended into 10 ml. of a 0.9% saline water to give a cell suspension. The same procedure was repeated for each hydantoin compound.

Mixtures of (1) 2.0 ml. of an aqueous substrate solution prepared by dissolving DL-5-(2-methylthioethyl)-hydantoin in a 0.1 M $NH_4Cl$-$NH_4OH$ buffer solution of pH 9.5 (substrate concentration: 2.0%) and (2) 2.0 ml. of the above cell suspension were prepared and placed in test tubes, respectively. The hydrolysis reaction was then carried out at 30° C. for one hour without shaking. Immediately after the completion of the reaction, 1.0 ml. of a 10% aqueous solution of trichloroacetic acid, 1.0 ml. of a 10% solution of p-dimethylaminobenzaldehyde in 6 N hydrochloric acid and 6.0 ml. of distilled water were added to each reaction mixture. Each resulting color-developed reaction mixture was centrifuged to remove insoluble materials, and the amounts of N-carbamoylmethionine produced in the reaction mixtures were colorimetrically determined by measuring the absorbance at 420 nm. As a Control, the above procedures were repeated except that no hydantoin compound was employed.

The amounts of N-carbamoylmethionine produced in the reaction mixtures and the amounts of N-carbamoylmethionine produced per dry weight (milligram) of cells are shown in Table 10.

From these results, it was confirmed that the hydantoin compounds added to the culture medium enhanced the asymmetrical hydrolysis ability of the microorganism.

TABLE 10

| Hydantoin compound | Amount of N-carbamoyl-methionine mg./ml. | Amount of N-carbamoyl-methionine per dry weight of cells mg./ml./mg. cells |
|---|---|---|
| Hydantoin | 3.0 | 1.0 |
| DL-5-methylhydantoin | 3.0 | 1.1 |
| DL-5-(2-methylthioethyl)hydantoin | 2.2 | 0.96 |
| Control | 2.0 | 0.70 |

What we claim is:

1. A process for preparing D-N-carbamoyl-α-amino acids having the following general formula:

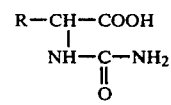

wherein R is an alkyl group, a substituted alkyl group, an aralkyl group, or a substituted aralkyl group, which comprises subjecting 5-substituted hydantoins having the following general formula:

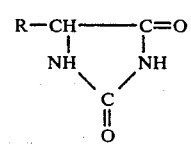

wherein R is as defined above, to the action of an enzyme which is in the form of a cultured broth containing microorganisms, or cells or treated cells of said microorganisms, wherein said microorganisms are selected from the group consisting of microorganisms belonging to genus, Achromobacter, Aerobacter, Aeromonas, Agrobacterium, Alcaligenes, Arthrobacter, Bacillus, Brevibacterium, Corynebacterium, Enterobacter, Erwinia, Escherichia, Klebsiella, Microbacterium, Micrococcus, Protaminobacter, Proteus, Sarcina, Serratia, Xanthomonas, Actinomyces, Actinoplanes, Mycobacterium, Nocardia, Streptomyces, Aspergillus, Paecilomyces, Penicillium, Candida, Pichia, Rhodotorula or Torulopsis, in an aqueous medium of pH 7 to 10, said enzyme being capable of hydrolyzing said 5-substituted hydantoins so as to substantially produce only D-forms of N-carbamoyl-α-amino acids, and recovering said D-N-carbamoyl-α-amino acids from the medium.

2. The process of claim 1, wherein said cells are intact cells or dried cells.

3. The process of claim 1, wherein said treated cells are crushed cells or cellular extract.

4. The process of claim 1, wherein said cells are immobilized.

5. The process of claim 1, wherein said treated cells are immobilized.

6. The process of claim 1, wherein said microorganism is those cultured in a culture medium containing a hydantoin compound to enhance the ability in asymmetrically hydrolyzing the hydantoin ring.

7. The process of claim 1, wherein said 5-substituted hydantoins are the DL-forms.

8. The process of claim 1, wherein said 5-substituted hydantoins are the L-forms.

* * * * *

UNITED STATES PATENT AND TRADEMARK OFFICE
CERTIFICATE OF CORRECTION

PATENT NO. : 4,237,227
DATED : December 2, 1980
INVENTOR(S) : Hideaki Yamada et al It is certified that error appears in the above-indentified patent and that said Letters Patent is hereby corrected as shown below:

On the title page:

In the heading, under [*] Notice: the date of "Jun. 13, 1992" after the words: "subsequent to" should read --Jun. 13, 1995--.

Signed and Sealed this

Twenty-fifth Day of July, 1995

Attest:

BRUCE LEHMAN

Attesting Officer

Commissioner of Patents and Trademarks